United States Patent

Magram

[11] Patent Number: 5,683,357
[45] Date of Patent: Nov. 4, 1997

[54] EXTERNAL CEREBROSPINAL FLUID DRAIN APPARATUS

[76] Inventor: Gary Magram, Apt. 108, 1 Gristmill Ct., Baltimore, Md. 21208

[21] Appl. No.: 566,068

[22] Filed: Dec. 1, 1995

[51] Int. Cl.$^6$ .................................................. A61M 5/00
[52] U.S. Cl. .................................................. 604/8; 604/9
[58] Field of Search ...................... 604/8–10, 317, 604/264; 128/748

[56] References Cited

U.S. PATENT DOCUMENTS

| | | | |
|---|---|---|---|
| 2,180,042 | 11/1939 | Ettinger | 604/9 |
| 3,601,128 | 8/1971 | Hakim | 604/9 |
| 3,889,687 | 6/1975 | Harris et al. | 28/350 |
| 4,601,724 | 7/1986 | Hooven et al. | 604/8 |
| 4,621,647 | 11/1986 | Loveland | 128/748 |
| 4,621,654 | 11/1986 | Holter | 137/38 |
| 4,769,002 | 9/1988 | Hooven | 604/9 |
| 5,405,316 | 4/1995 | Magram | 604/8 |

OTHER PUBLICATIONS

CSF–External Drainage and Monitoring Products Pudenz–Schulte Medical Corp., Goleta, CA, Brochure No. 10589–2, Dec. 1990.

Cordis ICP Monitoring and Drainage Sets . . . Cordis Corporation, Miami, FL, Brochure No. 152–3336–1, Sep., 1994.

*Primary Examiner*—John G. Weiss
*Assistant Examiner*—David J. Cho
*Attorney, Agent, or Firm*—Jeffrey C. Lew

[57] ABSTRACT

An apparatus is disclosed for draining cerebrospinal fluid from within a patient's body to a location outside the patient's body. The novel apparatus features a fluid accumulator located serially between the ventricular catheter and the external location. The accumulator holds an amount of fluid which can flow bidirectionally between the patient and the accumulator so as to replenish any excess fluid that surges from the patient due to sudden, unexpected movements, such as sneezing, coughing, suddenly changing from recumbent to upright position and systolic contractions. The accumulator serves to maintain the height of the fluid column in the apparatus at a steady level, despite the sudden movements. Thus the hydrostatic pressure exerted on the cerebrospinal spaces by the fluid, which controls intracranial pressure, remains substantially constant.

5 Claims, 4 Drawing Sheets

5,683,357

EXTERNAL CEREBROSPINAL FLUID DRAIN APPARATUS

FIELD OF THE INVENTION

This invention relates to a device for draining cerebrospinal fluid from a patient. More specifically, it relates to the use of an accumulator to drain cerebrospinal fluid from within the subarachnoid space to a container outside the body.

BACKGROUND OF THE INVENTION

The ventricles in the brain of an average human produce approximately 20 $cm^3$ of cerebrospinal fluid (CSF) per hour. In healthy individuals, CSF drains from the ventricles into the subarachnoid space and is absorbed by the arachnoid villi into the venous sinuses. The sinuses return the CSF mixed with blood to the heart. Some individuals suffer from disorders, such as hydrocephalus, in which the fluid stops absorbing normally and accumulates in the cranial cavity. Unless the fluid drains from the ventricles, intracranial pressure can build to life threatening levels. Often a shunt, e.g. a ventriculoperitoneal (VP) shunt, is implanted to drain excess CSF to another location inside the body. Occasionally, proper treatment calls for draining the fluid to an external receiver.

Historically, coughing or sneezing, sudden body movements, such as changing from recumbent to uptight position, and repetitive systolic contractions presented a significant problem for maintaining a desired intracranial pressure in a patient with a shunt or drain. These activities briefly compress organs within the cranial cavity which raises the fluid pressure in the subarachnoid space. For a short time high pressure produces high discharge flow which exceeds the rate at which the ventricles produce CSF. In a normal individual, CSF temporarily flows into the cervical subarachnoid space which can expand to accommodate the excess. Shortly thereafter, CSF flows back into the cranial cavity following the compression. However, in a shunt or drain patient, surplus CSF is drained from the cranial cavity and cannot be returned. Over time, a deficiency of CSF volume results and intracranial pressure generally declines to unhealthy levels.

The conventional method of compensating for the loss of fluid is for the attending physician to change the drainage rate periodically. Existing techniques to control CSF flow to a desired average rate are generally unsatisfactory. They require long term observation of the patient to accurately gauge CSF discharge flow rate in comparison to CSF production rate, which of course varies with the individual. Sometimes surgical intervention is needed to adjust the drainage rate, especially in the case of VP shunts.

A device for regulating intracranial pressure in a shunt patient by automatically compensating for sudden activities mentioned above is disclosed in U.S. Pat. No. 5,405,316. However, no apparatus for automatically maintaining a desired intracranial pressure in connection with an external drain is yet known in the art.

A conventional external drain typically includes an intraventricular catheter which connects to a fluid collection set. The set ordinarily has a first flexible tube for conducting CSF from the discharge end of the catheter to the top of a transparent, generally rigid, graduated receiver. Usually, the fluid drips into the receiver. The receiver connects by a bottom drain through a second flexible tube to a larger vessel, which can also be rigid but is frequently a distensible bag. Normally, a valve is provided in the second tube close to the bottom of the receiver so that flow to the collection vessel can be stopped temporarily while the rate of filling the container is measured. When the valve is opened, fluid resumes draining by gravity from the receiver into the vessel.

In such conventional external drain systems, CSF fills the first flexible tube with a column of fluid. The column exerts a hydrostatic pressure on the cranial cavity. The height of the column above the patient's head defines the intracranial pressure which must be developed to cause the fluid to drain. Therefore, the height of the first flexible tube necessary to allow the fluid to drip into the receiver sets the intracranial pressure. The attending physician adjusts intracranial pressure by raising or lowering the receiver relative to the elevation of the patient's head. The above described conventional CSF drainage system is unable to compensate for declining intracranial pressure due to sudden and temporary body disturbances. This is because the fluid is irreversibly removed as it drips into the receiver. Consequently, no CSF can flow back into the first flexible tube to refill the subarachnoid space when compression is relieved after a cough, suddenly sitting up or during diasystole, for example. Therefore, the hydrostatic pressure in the tube drops, which lowers intracranial pressure below normal and desirable level.

It is desirable to have an external CSF drainage apparatus which provides for a net discharge of fluid from the ventricles but which compensates for body motion to maintain a desired intracranial pressure.

SUMMARY OF THE INVENTION

The present invention relates to an improved external CSF drain apparatus which includes in serial connection between the ventricular catheter and the external receiver, a fluid accumulator capable of holding a volume of fluid. Fluid flow between the catheter and the accumulator is bidirectional. That is, CSF can drain from the ventricles, through the catheter and into the accumulator. However, following a sudden compression-decompression cycle, fluid can flow back from the accumulator into the catheter to replenish the subarachnoid inventory and restore intracranial pressure to the preselected value. Overflow from the accumulator is discharged to the receiver for disposal.

Accordingly, there is provided an external drain apparatus for draining cerebrospinal fluid from a patient's body to an external location outside the body, the apparatus comprising:

a catheter to receive the fluid from within the body, the catheter having a discharge end;

tubular means in fluid communication with the discharge end for conducting the fluid to the external location; and an accumulator in serial fluid communication intermediate the discharge end and the external location, the accumulator including:
  (1) a wall structure enclosing an inner volume to hold cerebrospinal fluid inside the accumulator, the fluid having a fluid level;
  (2) an overflow nozzle to discharge fluid from the accumulator to the external location, the overflow nozzle being in fluid communication with the inner volume and being at an elevation at least as high as the fluid level; and
  (3) an inlet pod being adapted to connect the accumulator to the tubular means to provide bidirectional flow of fluid between the inner volume below the fluid level and the discharge end.

There is also provided a method of draining cerebrospinal fluid from the subarachnoid space of a patient's body, such as through a ventricular tap, to a location outside the body, the process incorporating the use of a fluid accumulator which accepts fluid drained from the patient and returns fluid to the patient so as to maintain a desired intracranial pressure. More specifically, there is provided the method of draining cerebrospinal fluid from a patient's body to an external location outside the body, the method comprising the steps of:

(a) inserting into the patient a catheter to receive the fluid, the catheter having a discharge end;

(b) conducting the fluid to the external location through a fluid accumulator in serial fluid communication intermediate the discharge end and the external location, the accumulator including:

(1) a wall structure enclosing an inner volume to hold cerebrospinal fluid inside the accumulator, the fluid having a fluid level;

(2) an overflow nozzle to discharge fluid from the accumulator to the external location, the overflow nozzle being in fluid communication with the inner volume and being at an elevation at least as high as the fluid level; and (3) an inlet port being in fluid communication with the inner volume below the fluid level to provide bidirectional flow of fluid between the discharge end and the inner volume;

(c) determining a desired intracranial pressure for the patient;

(d) maintaining hydrostatic pressure of fluid in the accumulator effective to produce the desired intracranial pressure for the patient; and (e) collecting the fluid at the external location.

DETAILED DESCRIPTION

The present invention is based on the human physiological phenomenon that intracranial pressure fluctuates as the body moves. The activities of coughing, sneezing, breathing and changing position from sitting to standing, for example, briefly compress the intracranial contents, i.e., brain tissue, blood, and CSF. Consequently, subarachnoid fluid pressure increases and decreases. In a healthy patient, CSF may briefly flow to and from the cervical subarachnoid space so as to stabilize intracranial pressure. However, in a patient with an external drain, the route to the cervical subarachnoid space is usually blocked. Therefore, CSF surges out irreversibly through the drain instead.

The accumulator of the present invention serves as a substitute for the cervical subarachnoid reservoir. That is, the accumulator provides a reserve of CSF and it permits bidirectional flow between the patient and the fluid reserve. By bidirectional flow is meant that the subarachnoid fluid can flow from the patient to the accumulator, and the fluid in the accumulator can flow back to the subarachnoid space, depending on the pressure difference between the intracranial pressure and the hydrostatic pressure of the fluid column in the drain apparatus at any given time. Thus the novel apparatus permits the patient to maintain intracranial pressure at a steady value by allowing flow back to the patient. The steady value is governed by the hydrostatic pressure of fluid in the fluid reserve. Furthermore, the normal excess CSF is allowed to overflow from the accumulator into a fluid collector.

Figure 1:
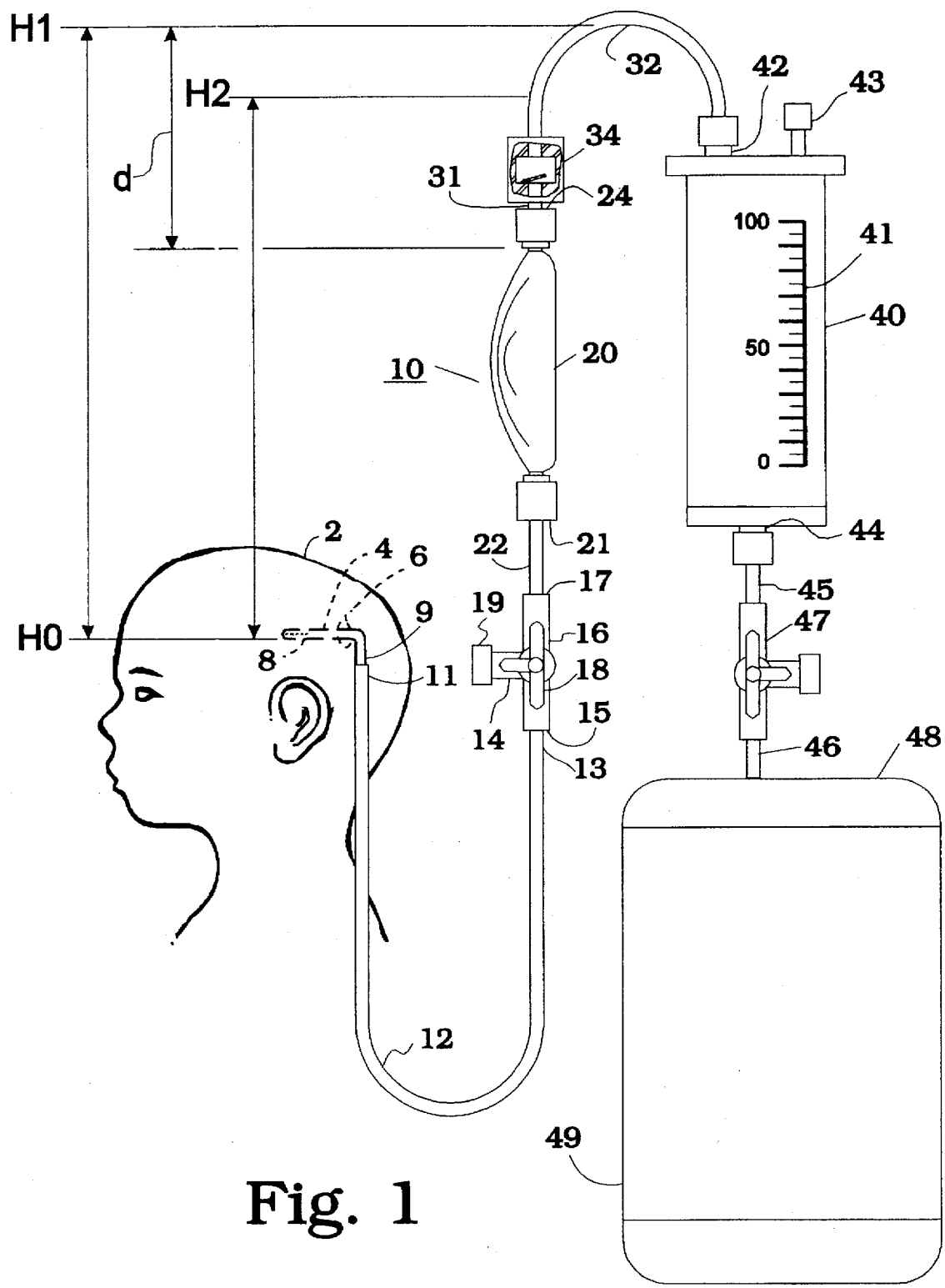
FIG. 1 is a side elevation view of one embodiment of an external cerebrospinal fluid drain apparatus according to the present invention in which the accumulator is a distensible bag.

The operation of the novel accumulator for an external cerebrospinal fluid drain can be understood with reference to FIG. 1. A ventricular catheter 4 of external cerebrospinal fluid drain apparatus 10 is inserted through burr hole 6 of skull 2 into a ventricle of the brain, not shown, of a patient whose disorder requires removal of excess CSF for extended durations. Near the end inserted in the ventricle, the catheter has holes 8 which provide openings for CSF to flow from the ventricle into the catheter. The catheter emerges from the burr hole and passes through the scalp, not shown, outside the body. At the discharge end 9, the catheter makes a fluid tight connection to one end 11 of a first flexible tube 12 provided to conduct fluid between the patient and accumulator 20. The second end 13 of the first flexible tube could be connected directly to the accumulator. However, in the illustrated embodiment, the second end makes a fluid tight connection with a port 15 of a valve 16. Any conventional block valve can be used, however, the illustrated embodiment employs a three-way, block and flow diversion valve. In normal operation, CSF flows from port 17 of the valve to the inlet port 21 of the accumulator 20 through another tube 22 provided for this purpose. To equal effect, the valve 16 could be close coupled to, or integral with, inlet port 21, so as to provide fluid communication between the patient and the accumulator.

The type of valve shown is well understood in the art. The three-way valve includes a side tap 14 which is shown capped by a removable, liquid tight cover 19. The internal mechanism of the three-way valve can be manipulated by handle 18 to permit passage of fluid between first flexible tube 12 and the accumulator; to block flow between the patient and the accumulator; or to allow infusion or withdrawal of fluid in the tube through side tap 14. Naturally, the cover should be removed first, to add or remove fluid from the side tap. It is also contemplated that the cover could have a puncturable, self-sealing membrane through which medicine or other therapeutic substance might be injected into the patient's CSF via syringe. Similarly, samples of the patient's CSF could be extracted via syringe inserted through such a membrane.

The accumulator can be a fluid containment vessel with elastically distensible walls and an exit port 24. By elastically distensible is meant that the walls of the accumulator are pliable and will stretch with negligible resistance so as to expand upon filling with a liquid up to a maximum volume. Exit port 24 of the overflow nozzle is in fluid tight connection with end 31 of a second flexible tube 32 which conducts fluid to a fluid collector 40. The fluid collector includes an entrance port 42 and an exit port 44. The bottom of the fluid collector is connected to a storage container 48 by tubes 45 and 46, and another three-way valve 47. Typically, fluid collector 40 is a rigid, generally transparent cylindrical vessel having entrance port 42 located at the top, however, the shape of the fluid collector is not critical. This arrangement enables CSF which overflows from the accumulator to drip into the collector in a manner that is visually perceptible for confirmation by the health care provider that the system is open to flow during the draining procedure.

In one method of use, three-way valve 47 is temporarily manipulated to block flow from leaving the collector. As drainage continues, the drops of fluid accumulate and coalesce in the collector to eventually form a liquid level. The meniscus of the liquid can be observed against an optional scale 41 provided for the purpose of measuring the volume of fluid in the collector. The scale can be calibrated in convenient volume units and can be integral to the wall of the collector or attached to an adjacent frame to which the collector is mounted. Over time, the rate of drainage can be determined by dividing the total volume of fluid collected by the measured duration of collection.

As CSF enters the collector it displaces vapor which is exhausted to ambient atmosphere through vent 43. The atmospheric vent assures that vapor within the collector equilibrates to pressure outside the collector. Hence vapor in the collector does not compress to exert a superatmospheric back pressure on top of the column of fluid in the drain apparatus. The vent can be equipped with an optional filter, not shown, to prevent accidental cross contamination between the environment and the collected fluid.

After inventory in the fluid collector has reached capacity, valve 47 can be opened to drain the collected fluid into storage container 48. In the illustrated embodiment, storage container 48 includes a preferably transparent, and generally distensible bag 49. Initially, the bag is empty and completely collapsed. The walls distend to accept fluid entering the bag. Because no air is displaced during filling, the bag does not need a vent. The storage container may have a connector, not shown, to allow disconnection from three-way valve 47, thereby permitting the container to be removed for disposal and replacement. While the storage container is disconnected, flow can be blocked or diverted through three-way valve 47 to a secondary receiver.

Elevation of the components of the ventricular drain apparatus relative to the height of the patient, particularly of the patient's head, is very important. As mentioned, the height of fluid column in the flexible tubes and accumulator between the patient and the fluid collector defines the back pressure exerted on the patients intracranial cavity. More specifically, the differential between the height of the fluid column and the ventricular catheter determines intracranial pressure. In FIG. 1, reference symbol H0 represents the height of the ventricular catheter. Reference symbol H1 represents the height of the top of the fluid column inside the second flexible tube. When the fluid level in the second flexible tube attains height H1, additional fluid forces the excess to pour over the crest of the bend in the tube and to drip into the fluid collector. Hence the distance H1 - H0 determines the hydrostatic pressure against which the intracranial pressure must pump in order to expel fluid into the collector. The crest of the flexible tube 32 thus acts as a weir type overflow nozzle which defines the elevation of H1.

In a conventional external drain no accumulator is present. When the patient's intracranial contents are suddenly compressed, the increased pressure displaces an excess of CSF over the crest and into the collector. Soon thereafter, the intracranial contents return to near the pre-compressed state. Fluid will flow back into the subarachnoid space from the tube. However, no fluid from the collector can return to tube 32. Consequently, fluid in the tube will drop to a low level, H2. Because the hydrostatic pressure H2-H0 is less than H1-H0, intracranial pressure will be lower. If the patient moves again, it is possible for more fluid to overflow into the collector, leaving less in the tube and thus lowering intracranial pressure still further.

The presence of an accumulator with elastically distensible walls solves the problem just mentioned. The accumulator can be filled in advance with fluid which can be the patient's own CSF or a synthetic substitute, for example, sterile saline solution. As the accumulator is filled, the pouch inflates to accommodate the entering fluid. Ultimately, the inflation reaches a maximum defined by the elasticity and strength of the wall material. Thereafter, more fluid added to the apparatus raises the level in the second flexible tube until the excess overflows into the fluid collector. If the patient moves suddenly in such a way as to temporarily increase intracranial pressure, excess fluid will overflow into the fluid collector. However, when the condition causing increased intracranial pressure is relieved, some fluid held in the accumulator will flow back into the subarachnoid space. The accumulator inventory will temporarily reduce by an amount substantially equal to the amount of fluid returned to the patient. Meanwhile, the level of the fluid column in the second flexible tube will remain substantially constant, thereby maintaining a steady intracranial pressure.

The accumulator according to this invention should have a liquid capacity greater than the amount of CSF that is expected to surge as a result of the patient's sudden movements. The liquid capacity should be at least about 20 cm$^3$ and preferably, at least about 50 cm$^3$. The upper limit of the liquid capacity is not critical, however, it is recognized that the larger the volume, the greater amount of fluid should be placed in the accumulator initially.

In CSF drain sets, medicine is sometimes added to the fluid in the flexible tube to achieve a therapeutic effect. Because the quantity of fluid resident in the tube is usually quite small, a very small amount of medicine normally must be added with great precision, which is relatively difficult to do. The medicine also tends to purge from the apparatus soon after administration. In contrast, to obtain similar therapeutic concentrations, larger absolute amounts of medicine can be added to the larger body of fluid in the accumulator of the novel drain apparatus. This feature renders easier the task of administering a precise quantity of medicine. Moreover, the medicine will purge more slowly from the novel drain apparatus due to the inventory of fluid in the accumulator. Hence the present invention overcomes additional shortcomings of conventional technology.

The wall structure of the accumulator is important to the operation of the basic embodiment of this invention shown in FIG. 1. The walls are generally of thin, pliable membrane, preferably of a polymer, such as polyethylene, polypropylene, polyester and polyetherester. The polymer can be formed as sheets and laminated to create an inflatable pouch. The walls are capable of reversible distention to inflate the pouch with negligible resistance up to a maximum capacity. That is, the walls will not exert more than a negligible back pressure on fluid flowing into the pouch. Similarly, on emptying, the pouch will deflate with little resistance from the walls. The accumulator is sterilized, evacuated of air and fully collapsed prior to first use. By methods known in the art, the pouch can be fitted with inlet and outlet nozzles and appropriate connectors for coupling the accumulator to conventional plastic, ventricular drain tubing.

Figure 5:
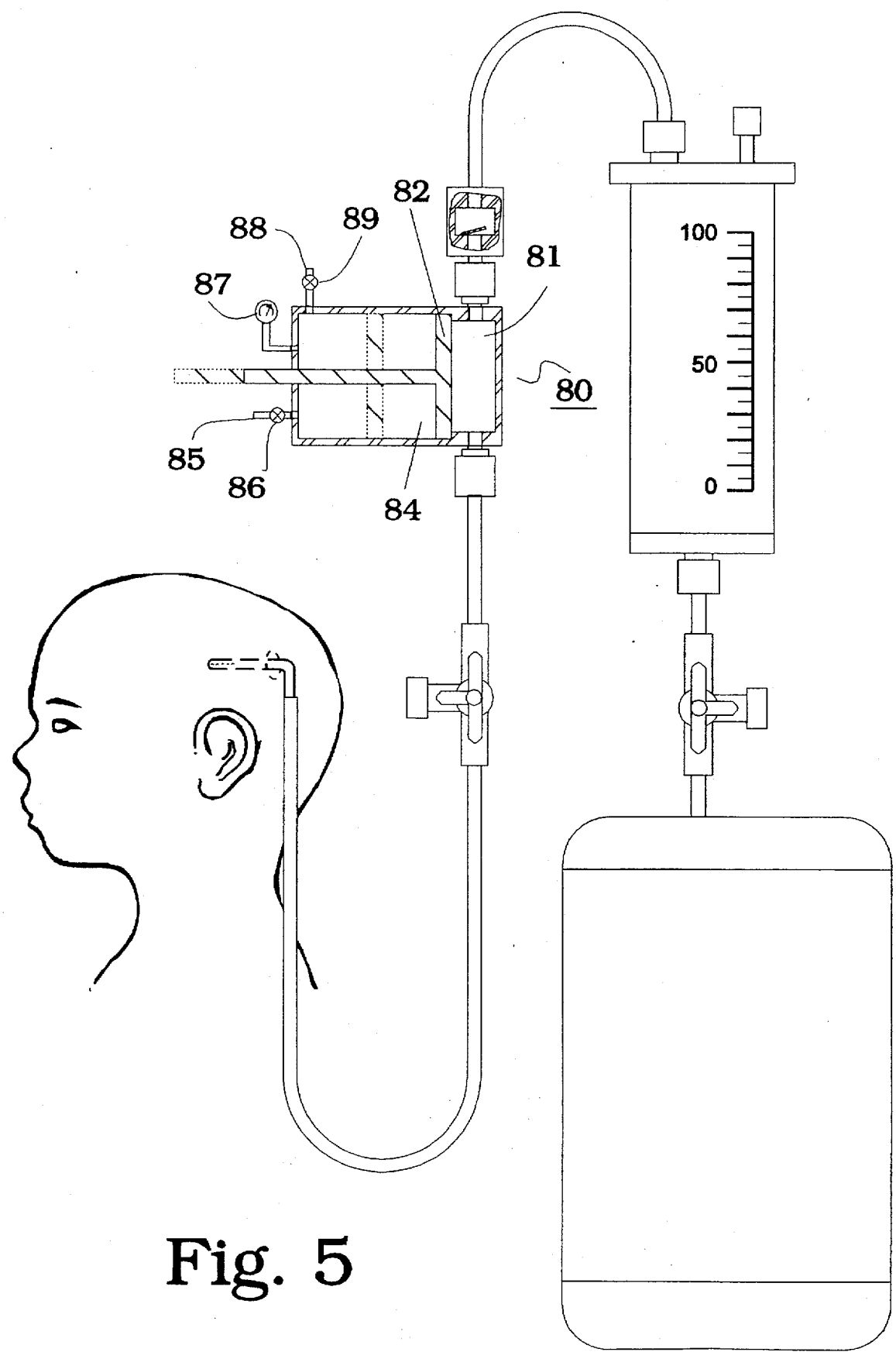
FIG. 5 is a side elevation view of an embodiment of an external cerebrospinal fluid drain apparatus of this invention wherein the wall structure of the accumulator includes a moveable piston.

As seen in FIG. 5., the accumulator 80 for a different embodiment of the novel drain apparatus can be constructed with a CSF containment space 81 bounded by at least one moveable wall 82, such as a piston, as shown, or a bellows. The moveable wall is forced against the CSF by a pressure activated mechanism, such as a fixed mass of a reversibly compressible substance, for example, a compressible gas, in a confined space, 84, or a spring. As the CSF from the patient fills the containment space, it pushes against the moveable wall 82, which gives way to expand the capacity of the containment space to accommodate the added CSF, as shown in phantom. However, as more CSF enters the containment space, the pressure activated mechanism exerts increasing force to oppose further accumulator capacity expansion. Eventually, the CSF pressure equilibrates with the opposing force from the pressure activated mechanism. At this point the CSF containment space ceases to expand further and CSF overflows from the accumulator into a fluid collector. The ultimate capacity of the accumulator and thus the effective intracranial pressure can be set by manipulating the pressure activated mechanism. For example, the pressure of the reversible compressible substance can be chosen to provide an appropriate opposing force necessary to maintain a desired intracranial pressure. By manipulating valve 86, the reversibly compressible substance from a source not shown, can be charged to the confined space through nozzle 85 until the desired pressure is observed on gauge 87. By manipulating valve 89, excess reversibly compressible substance can be bled from the confinement space through nozzle 88 to a receiving location, not shown. Similarly, the load on the spring of a spring type pressure activated mechanism can be adjusted to produce the desired intracranial pressure.

Figure 4:
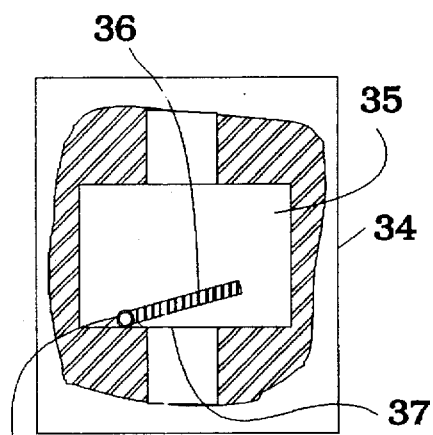
FIG. 4 is a partially cut away view of a back pressure valve for optional use in connection with the novel external cerebrospinal fluid drain apparatus.

Referring to FIGS. 1 and 5, the novel external drain apparatus can include an optional back pressure valve 34, shown partially cut away, downstream of the accumulator. Any conventional type of back pressure valve can be used, such as a ball type. A flap type valve is shown in greater detail in FIG. 4. This valve has an interior cavity 35 in fluid communication with inside of the second flexible tube. A weighted flap 36 is normally seated against the opening 37 leading from the accumulator into the interior cavity. When pressure within the accumulator is sufficient to overcome the sealing force, the flap swings on pivot 38 to discharge fluid to the collector. The purpose of the back pressure valve is to set the back pressure which the CSF must overcome to drain out of the patient.

It should be clear from the description above, that the locations of the fluid collector and the storage container are normally unimportant. For proper operation of the external cerebrospinal fluid drain, however, the hydrostatic pressure exerted by the fluid column in the flexible tube and accumulator, and/or the back pressure valve, should be slightly higher than that of the ventricular tap.

The stability of intracranial pressure can be optimized by minimizing the vertical distance, d, of the crest of second flexible tube above the top of the accumulator, or by increasing the diameter of the second flexible tube. These features will help assure that level in the second flexible tube will not radically change when fluid returns to the patient after an episode of sudden movement.

Figure 2:
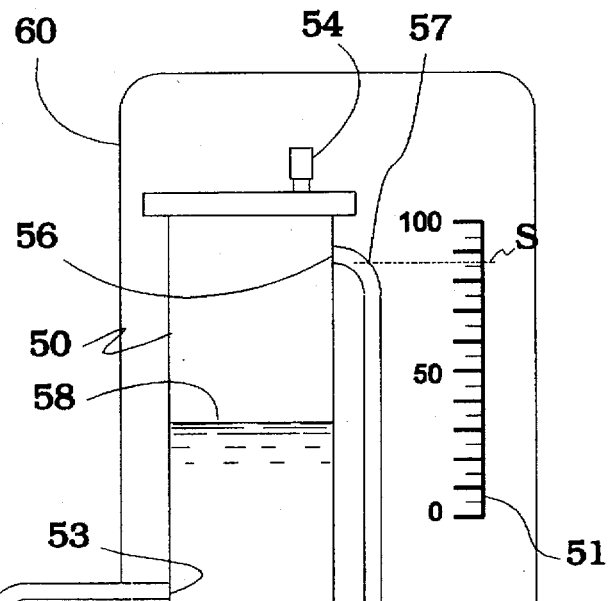
FIG. 2 is a side elevation view of another embodiment of an external cerebrospinal fluid drain apparatus of the present invention, wherein the accumulator is a rigid fluid collector.
Figure 2:
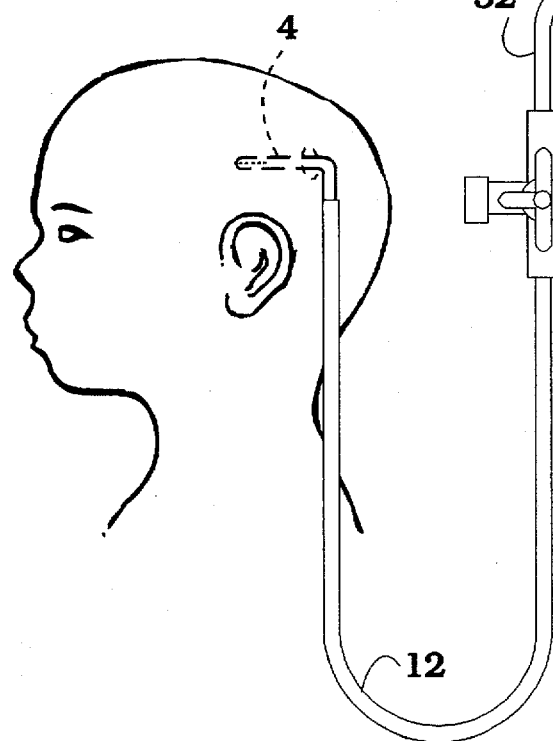

A different embodiment of the novel ventricular drain apparatus is shown in FIG. 2. Like elements in the figures are provided with the same reference designations. In this embodiment, the fluid accumulation function is performed in fluid collector 50. CSF from the ventricular catheter 4 is supplied through first flexible tube 12, valve 16, and second flexible tube 52 to the bottom of the fluid collector. The fluid thus defines a vapor-liquid interface 58 inside the collector. For proper operation, it is important that the discharge end 53 of the second flexible tube is submerged in the fluid. When this occurs, fluid will be available to flow back into the second flexible tube to replenish any excess fluid discharged due to sudden body movement of the patient.

As additional fluid enters the fluid collector, vapor above the liquid is displaced. Vent 54 is provided to discharge displaced vapor to equilibrate pressure inside the collector with that of the ambient atmosphere. An optional filter, not shown, can be used in connection with the vent to prevent cross contamination between the fluid and the atmosphere. The vapor-liquid interface 58 will continue to rise until it eventually attains the level of the overflow nozzle 56. Thereafter fluid will commence to pour into the discharge tube 57, and exit through port 55 and valve 47 into storage container 48. The filling process can be accelerated by charging natural or synthetic (e.g., sterile saline solution) to the collector to raise the interface level near the overflow nozzle. It is apparent from FIG. 2, that intracranial pressure will be determined by the height of the column of fluid above the ventricular catheter in the flexible tubes, 12 and 52, and the fluid collector. Hence, intracranial pressure is governed by the elevation of the overflow nozzle. For convenience, the collector and connected parts can be attached to a frame 60 which is mounted at a fixed elevation relative to the patient. For example, the frame can be hung from an intravenous fluid suspension pole. The frame is marked with a scale 51 graduated to a desirable range of vertical distances. The collector is attached to the frame so as to permit the collector to reposition vertically relative to the frame. When the collector is placed at a desired elevation, it can be fixed in position. Mechanisms for slidably attaching a fluid collector to a frame are well known in the art. See the Cordis EDS Mounting Card, available as catalog no. 910-123C from Cordis Corporation, Miami, Fla. Accordingly, the health care provider can adjust the vertical position of the collector so that the level of the overflow nozzle 56 equals a selected scale setting, S, which corresponds to a desired intracranial pressure.

Once set, the novel ventricular drain apparatus will maintain a stable intracranial pressure regardless of sudden movement by the patient. If the patient coughs, sneezes or otherwise moves in such a manner as to temporarily compress the subarachnoid space, excess fluid will instantaneously flow into the collector. Some fluid will flow into discharge tube 57. However, soon after, when the patient recovers, fluid from the collector can return to the patient to refill the decompressed intracranial volume. Moreover, the hydrostatic pressure exerted on the patient will remain stable because the level of fluid in the tubes, 12 and 52, and the collector will have stayed constant.

Better results are contemplated when the cross section area of the collector at about the elevation of the overflow nozzle is substantially greater than the cross section area of the lumen of the flexible tubes and when the liquid volume in the collector is large compared to the amount of excess fluid which briefly surges into the discharge tube. The cross section area of the collector is preferably at least about 10 times, and more preferably at least about 20 times as large as the cross section of the lumen of the flexible tubes. Preferably, the liquid capacity of the collector at over flow condition should be at least about 20 cm³ and more preferably, at least about 50 cm³. Under these conditions, the level of the vapor liquid interface will drop only negligibly, if at all. Therefore, the height of the fluid column which governs intracranial pressure will remain virtually constant.

As shown in FIG. 2, second flexible tube enters the collector from the side. If necessary to completely drain the collector, a drain nozzle 72 equipped with drain valve 74 can be provided.

Figure 3:
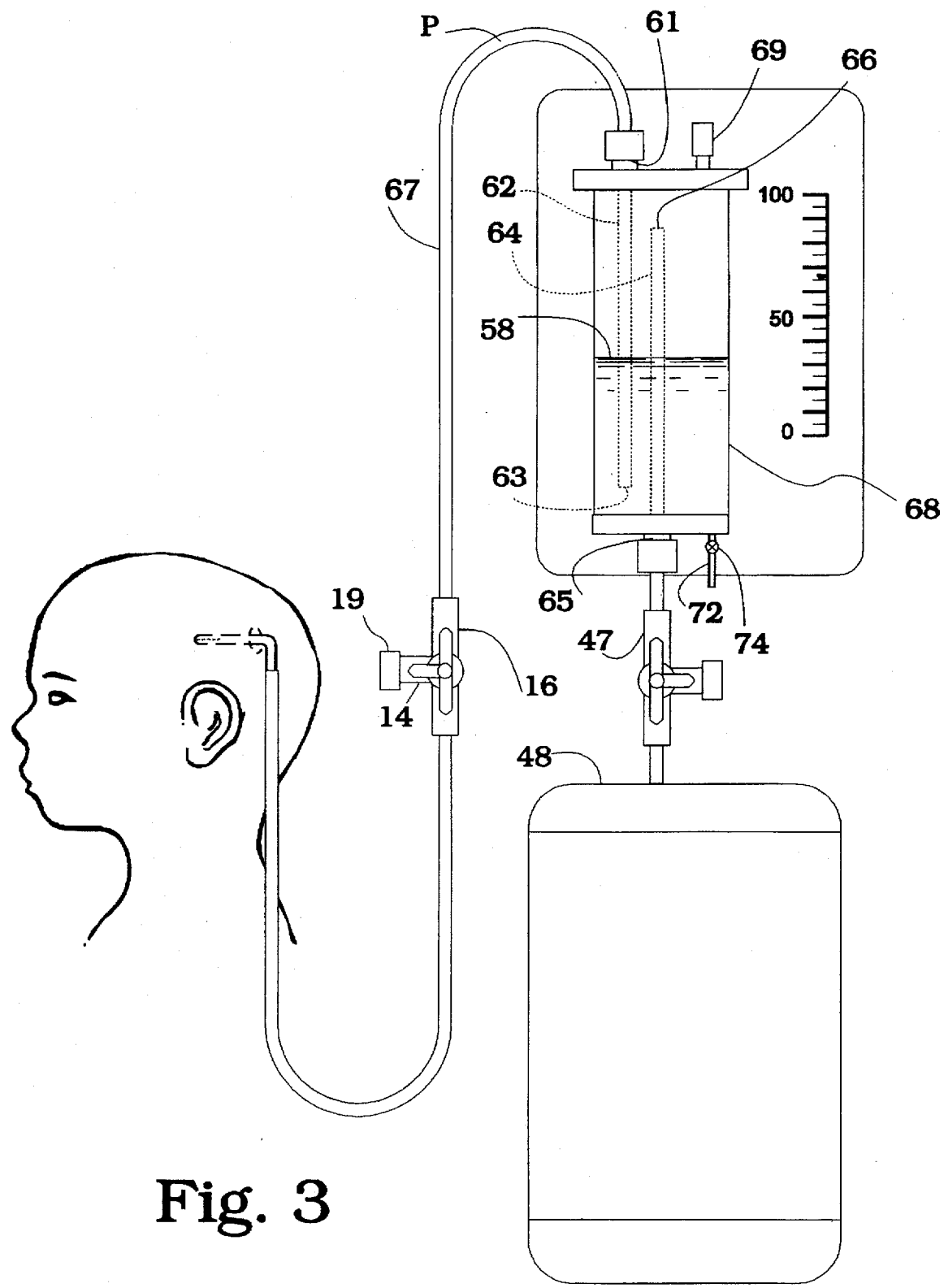
FIG. 3 is a side elevation view of a different embodiment of an external cerebrospinal fluid drain apparatus of the present invention, wherein the accumulator includes a dip tube and a stand tube.

A different embodiment of the ventricular drain apparatus according to the present invention is shown in FIG. 3. Like elements bear like reference numerals to the preceding figures. In this embodiment, second flexible tube 67 discharges into the fluid collector through port 61 and internal dip tube 62. Similarly, collector exit port 65 is equipped with an internal stand tube 64 which defines the elevation of the overflow nozzle 66. As fluid enters the collector, level rises to submerge open end 63 of the dip tube. Addition of more fluid causes the level to rise further until liquid pours into the stand tube through overflow nozzle 66. Thus the overflow nozzle defines the height of the fluid column which determines intracranial pressure.

The dip tube assures that the open end 63, which is effectively the discharge of the second flexible tube, is below the vapor liquid interface, 58, even though the second flexible tube enters from above the fluid collector. Because the discharge end of the second flexible tube is submerged, it is possible for fluid to return to the patient after a compression-decompression episode, provided that the crest of the second flexible tube is filled with liquid. Normally, fluid draining from the patient will flow over the crest leaving an air bubble at the high point, P, inside the tube. However, by carrying out the following steps, the second flexible tube can be fully charged with liquid:

(1) Charge fluid to accumulator 68 to submerge opening 63.

(2) Remove cap 19 from side tap 14 of valve 16 and connect one end of a new flexible tube, not shown, to the side port of valve 16. Fluid will be drained from the second flexible tube through the side tap. Therefore, connect the second end of the new flexible tube to a storage container. This fluid can be drained to container 48 by connecting the second end of the new tube to the side tap of valve 47, for example.

(3) Stop flow through collector exit pod 65 by manipulating valve 47.

(4) Blow gas, such as nitrogen or air, under slight pressure into the collector through vent 69 to force liquid into open end 63, up through dip tube 62, through second flexible tube 67 and out side tap 14.

(5) When all vapor has been purged from second flexible tube 67, remove the gas supply and vent the collector to atmosphere.

(6) Manipulate valve 16 to reestablish flow between the patient and the collector.

A drain nozzle 72 with drain valve 74 is preferably included in order to completely drain fluid from the collector. Operation and features of the ventricular drain apparatus illustrated in FIG. 3 are otherwise substantially similar to those of the embodiment of FIG. 2.

The primary advantage of a dip tube and stand tube configuration as shown in FIG. 3 is that existing types of external drain apparatus perhaps can be most easily modified in this manner to provide the benefits of the present invention. That is, conventional external cerebrospinal fluid drain sets typically drip CSF from the patient into a fluid collector through a top fill fitting. Such conventional drain sets also usually withdraw CSF from the collector through a bottom drain pod. By simply adding a dip tube and a stand tube, existing sets can provide the function of a fluid accumulator to improve control of intracranial pressure as described above.

In use, the novel external CSF drain apparatus will be used as follows: A patient diagnosed as having need of an external drain will be tapped and have a ventricular catheter inserted according to known procedures. A flexible tube will be connected between the discharge end of the catheter and the accumulator. The accumulator can be pre-loaded with natural or synthetic CSF (e.g., saline) to establish a fluid level in the accumulator above the inlet port and at or below the overflow nozzle. The overflow nozzle can be connected to a receiving container to catch excess fluid. By known methods, the physician will determine the desired intracranial pressure needed by the patient. The physician can then determine the hydrostatic pressure of the column of fluid in the drain apparatus necessary to induce the desired intracranial pressure in the ventricular catheter. Then the accumulator can be set to the appropriate elevation to produce the desired hydrostatic pressure. In a drain apparatus of FIGS. 1–3, the hydrostatic pressure will be governed by the height of the overflow nozzle. In a drain apparatus with a moveable wall, as in FIG. 5, the hydrostatic pressure will be set by the pressure activated mechanism. For example, the pressure of the compressible gas in FIG. 5 can be pre-loaded to the hydrostatic pressure by charging gas to the compartment behind the piston until the pressure gauge 86 indicates the desired value. If necessary, excess gas can be bled from the gas compartment through vent 87 by valve 88 to reduce the piston loading pressure.

Although specific forms of the invention have been selected for illustration in the drawings, and the preceding description is drawn in specific terms for the purpose of describing these forms of the invention, this description is not intended to limit the scope of the invention which is defined in the claims. For example, the external cerebrospinal fluid drain apparatus can be used to drain CSF through a lumbar tap.

I claim:

1. An external drain apparatus for draining cerebrospinal fluid from a patient's body to an external location outside the body, the apparatus comprising:

a catheter to receive the fluid from within the body, the catheter having a discharge end;

tubular means in fluid communication with the discharge end for conducting the fluid from the catheter; and an accumulator in serial fluid communication with the tubular means, the accumulator including:

(1) a wall structure enclosing an inner volume to hold an inventory of cerebrospinal fluid inside the accumulator, the inventory having a fluid level;

(2) an overflow nozzle to discharge fluid from the accumulator to the external location, the overflow nozzle being in fluid communication with the inner volume and being at an elevation at least as high as the fluid level; and (3) an inlet port below the fluid level being adapted to connect the accumulator to the tubular means to provide bidirectional flow of fluid between the inventory and the discharge end.

2. The external drain apparatus of claim 1 wherein the wall structure is a rigid fluid collector including a vent in vapor communication between ambient atmosphere and the inner volume above the fluid level.

3. The external drain apparatus of claim 2 wherein the tubular means is a flexible tube having a lumen cross section area and wherein the inner volume has a volume cross section area at about the elevation of the overflow nozzle being substantially greater than the lumen cross section area.

4. The external drain apparatus of claim 3 wherein the volume cross section area is at least about 10 times the lumen cross section area.

5. The external drain apparatus of claim 2 wherein the overflow nozzle is a stand tube that extends from the bottom of the accumulator into the inner volume to an elevation defining the fluid level, and wherein the inlet port includes a dip tube that extends from the top of the accumulator to the inner volume below the fluid level.

* * * * *

UNITED STATES PATENT AND TRADEMARK OFFICE
CERTIFICATE OF CORRECTION

PATENT NO. : 5,683,357
DATED : November 4, 1997
INVENTOR(S) : Gary Magram

It is certified that error appears in the above-identified patent and that said Letters Patent is hereby corrected as shown below:

In column 2, line 64, delete "pod" and substitute -- port -- therefor.
In column 10, line 3, delete "pod" and substitute -- port -- therefor.

Signed and Sealed this

Seventeenth Day of February, 1998

Attest:

BRUCE LEHMAN

Attesting Officer    Commissioner of Patents and Trademarks